(12) United States Patent
Herlitz

(10) Patent No.: US 8,977,572 B2
(45) Date of Patent: Mar. 10, 2015

(54) SYSTEMS AND METHODS FOR PATIENT-CONTROLLED, ENCRYPTED, CONSOLIDATED MEDICAL RECORDS

(75) Inventor: Sten Herlitz, Boston, MA (US)

(73) Assignee: General Electric Company, Schenectady, NY (US)

( * ) Notice: Subject to any disclaimer, the term of this patent is extended or adjusted under 35 U.S.C. 154(b) by 1203 days.

(21) Appl. No.: 12/183,258

(22) Filed: Jul. 31, 2008

(65) Prior Publication Data

US 2010/0030690 A1    Feb. 4, 2010

(51) Int. Cl.
| | | |
|---|---|---|
| G06Q 99/00 | (2006.01) | |
| G06Q 50/22 | (2012.01) | |
| G06F 19/00 | (2011.01) | |
| G06F 21/62 | (2013.01) | |
| G06Q 10/10 | (2012.01) | |
| H04L 9/32 | (2006.01) | |

(52) U.S. Cl.
CPC ............ *G06Q 50/22* (2013.01); *G06Q 2220/10* (2013.01); *G06F 19/322* (2013.01); *G06F 21/6245* (2013.01); *G06Q 10/10* (2013.01); *H04L 9/3226* (2013.01); *H04L 2209/88* (2013.01)
USPC .......................................................... 705/51

(58) Field of Classification Search
USPC .......................................................... 705/51
See application file for complete search history.

(56) References Cited

U.S. PATENT DOCUMENTS

| | | | |
|---|---|---|---|
| 6,484,260 B1 * | 11/2002 | Scott et al. | 713/186 |
| 7,058,696 B1 * | 6/2006 | Phillips et al. | 709/217 |
| 8,566,247 B1 * | 10/2013 | Nagel et al. | 705/59 |
| 2003/0074564 A1 * | 4/2003 | Peterson | 713/182 |
| 2005/0125258 A1 * | 6/2005 | Yellin et al. | 705/3 |
| 2006/0031101 A1 * | 2/2006 | Ross | 705/3 |
| 2009/0037224 A1 * | 2/2009 | Raduchel | 705/3 |
| 2009/0055924 A1 * | 2/2009 | Trotter | 726/20 |
| 2009/0077024 A1 * | 3/2009 | Abraham-Fuchs et al. | 707/3 |
| 2009/0093688 A1 * | 4/2009 | Mathur | 600/300 |
| 2009/0125326 A1 * | 5/2009 | Wasson et al. | 705/2 |

* cited by examiner

*Primary Examiner* — James D Nigh
(74) *Attorney, Agent, or Firm* — Hanley, Flight and Zimmerman, LLC

(57) ABSTRACT

Certain embodiments of the present invention provide systems and methods for managing medical information. Certain embodiments provide a system for managing medical information. The system includes a data center for centrally storing patient medical data as unstructured encrypted data. The system also includes a patient interface providing storage and retrieval of patient medical data at the data center. The patient interface communicates with the data center to transmit encrypted patient medical data to the data center. The encrypted patient medical data is encrypted at the patient interface using a patient encryption key assigned to a patient. The patient interface is further configured to receive encrypted patient medical data from the data center and decrypt the patient medical data using the patient encryption key assigned to the patient.

11 Claims, 8 Drawing Sheets

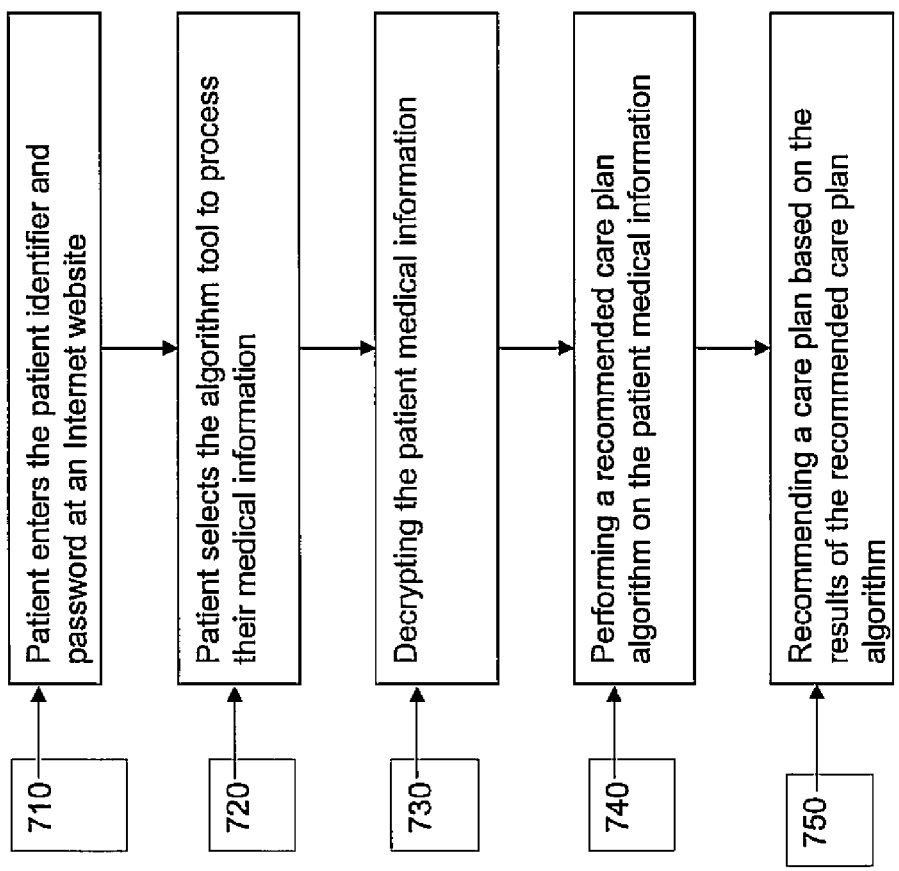

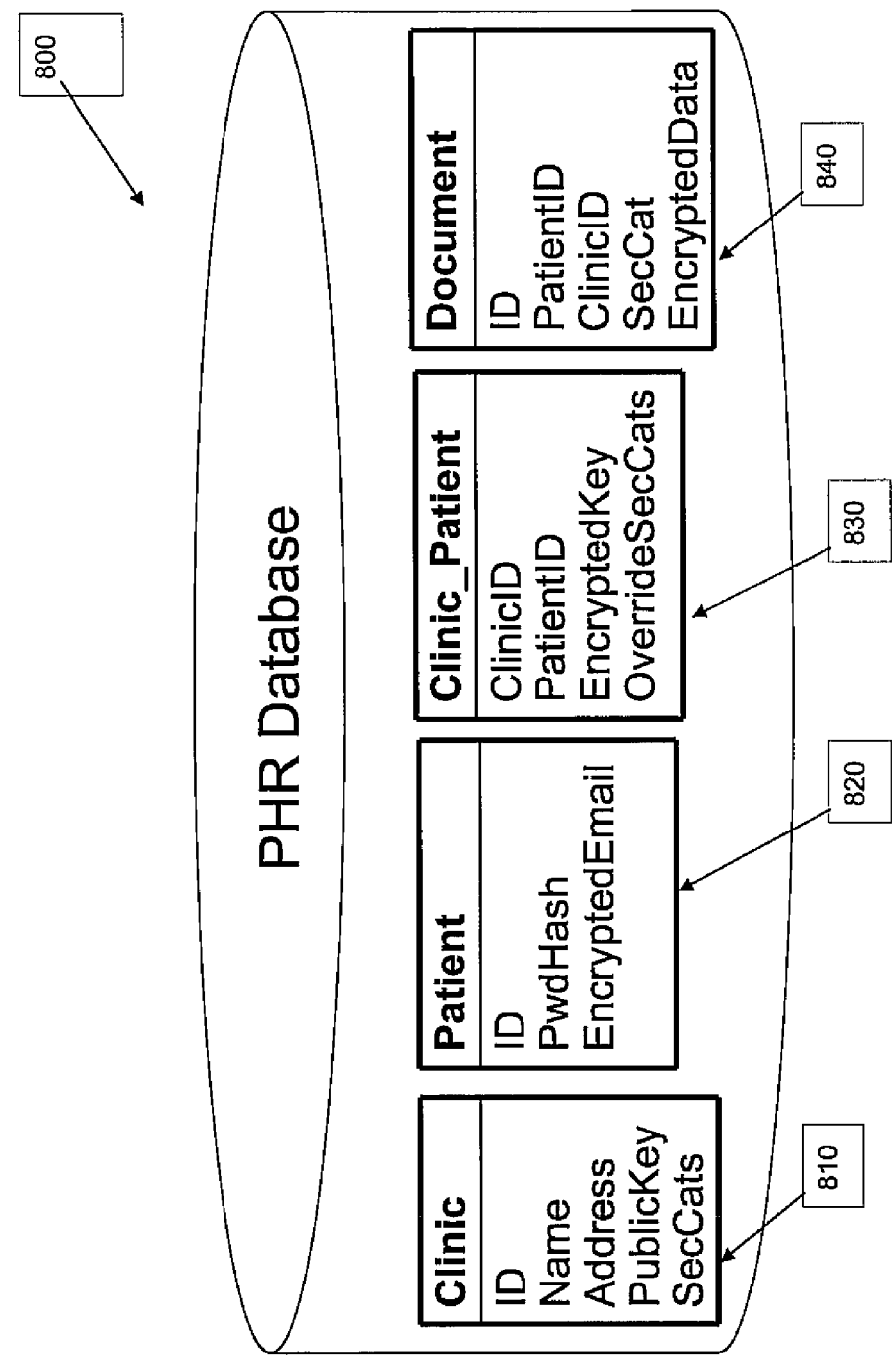

SYSTEMS AND METHODS FOR PATIENT-CONTROLLED, ENCRYPTED, CONSOLIDATED MEDICAL RECORDS

RELATED APPLICATION

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to a system and method for managing health care information. Particularly, the present invention relates to a system and method for centrally storing patient medical record data in encrypted form and for providing patient specific health care management.

In the current medical environment, access to patient medical records is cumbersome and fragmented. Typically, medical records are maintained at individual clinics. If a patient visits more than one clinic, a patient may have a plurality of medical records. For example, a patient may visit a first clinic and create a first medical record and the patient may subsequently visit a second clinic and create a second medical record. If the second clinic does not have access to the first medical record, the examination and diagnosis at the second clinic may be duplicative and inefficient.

The lack of comprehensive medical records is also duplicative and inefficient for the patient. For example, a patient typically fills out similar forms at each clinic the patient attends. The patient may fill out a form with the patient's medical history, various conditions, allergies, heredity information, or other information. The individual clinic then maintains their own record for the patient. As a patient may visit a plurality of clinics throughout their life, the patient may repeatedly fill out the same information. In some circumstances, the patient may not fill out the same information and the various medical records at different clinics may contain partial and/or out-of-date information.

In addition, the decentralized nature of patient medical record information is perpetuated by entities other than medical clinics. For example, medical record information may be maintained by insurance entities, pharmaceutical entities, and/or laboratory entities. An update of the patient medical record at any one of these entities does not ensure the other entities are updated. Accordingly, the patient medical record information differs depending on the entity. Accordingly, it is difficult to locate a medical record that is completely up-to-date and a treating physician may not be able to obtain a complete picture of a patient's health prior to treatment.

Moreover, the decentralized nature of patient medical record information typically does not allow a patient to access their medical records. A patient cannot review a comprehensive report of their medical history and various conditions. The patient generally does not have the ability to access or update their medical records. In addition, the patient does not have the ability to restrict access to their medical records.

As a consequence of patient information being decentralized and a patient not having access to their patient medical record information, the information available to a patient regarding their health status is typically of a general nature. For example, a patient has limited sources of medical information. One of the sources a patient may attempt to gather information from is the Internet. A patient may search for medical information on the Internet and find various web sites providing general information about the condition. Some of the information may be applicable to the context of the patient and some of the information may not. A patient may have difficulty in sorting through the available information and determining what information is applicable to their circumstances. A system and method is needed to centralize patient medical record information and allow a patient to view medical information in a personalized context.

SUMMARY OF THE INVENTION

Certain embodiments of the present invention provide systems and methods for managing medical information.

Certain embodiments provide a system for managing medical information. The system includes a data center for centrally storing patient medical data as unstructured encrypted data. The system also includes a patient interface providing storage and retrieval of patient medical data at the data center. The patient interface communicates with the data center to transmit encrypted patient medical data to the data center. The encrypted patient medical data is encrypted at the patient interface using a patient encryption key assigned to a patient. The patient interface is further configured to receive encrypted patient medical data from the data center and decrypt the patient medical data using the patient encryption key assigned to the patient.

Certain embodiments provide a method for managing medical information. The method includes receiving a patient identifier and password to authenticate a patient at a patient interface. The method also includes receiving a command to process medical information for the patient with an algorithm, wherein the medical information is received from a central data store. Additionally, the method includes decrypting the medical information of the patient at the patient interface using a patient encryption key. The method further includes processing the medical information of the patient at the patient interface with an algorithm. In addition, the method includes recommending an output based on the results of the algorithm.

Certain embodiments provide a method for a patient to access the medical record data of the patient. The method includes receiving a patient identifier and password to authenticate the patient. The method additionally includes receiving the encrypted medical record data from an external source and saving the encrypted medical record data to a local memory. The method further includes receiving a unique encryption key assigned to the patient. The method also includes decrypting the encrypted medical record data with the unique encryption key assigned to the patient. In addition, the method includes displaying the medical record data to the patient and optionally receiving changes to the medical record data from the patient. The method includes encrypting at least the changes to the medical record data with the unique encryption key assigned to the patient. The method further includes communicating at least the encrypted changes to the medical record data to the external source.

Certain embodiments provide a method for registering a patient for accessing the medical record data of the patient. The method includes creating a unique patient identifier and assigning an encryption key to the patient. The method additionally includes storing a mapping of the unique patient identifier to a local clinic patient identification of a clinic. The method further includes transferring the unique patient identifier and the encryption key assigned to the patient to a token. The method also includes associating the patient with the clinic by creating a clinic-specific representation of the encryption key. In addition, the method includes transmitting the clinic-specific representation of the encryption key and the unique patient identifier to an external memory. The method further includes encrypting the medical record data using the encryption key assigned to the patient. The method includes transmitting the medical record data, wherein the medical record data is encrypted with the encryption key assigned to the patient.

Certain embodiments provide a method for receiving and transmitting updated information for medical record data of a patient from a patient interface to a data center. The method includes identifying a unique identifier and assigned encryption key of the patient from a token of the patient, wherein the identification is performed at an associated medical clinic. The method further includes accessing the encrypted medical records of the patient stored on external memory and receiving updated information for the medical record of the patient. The method additionally includes decrypting the updated information with the assigned encryption key at the associated medical clinic. The method also includes updating the medical record data of the patient that is stored locally with the decrypted updated information. In addition, the method includes encrypting new patient information with the assigned encryption key of the patient. The method further includes transmitting the encrypted new patient information to the external memory.

Certain embodiments provide a method for accessing the medical records of a patient upon an emergency encounter. The method includes identifying a unique identifier and assigned encryption key of the patient from a token of the patient. The method additionally includes sending an emergency request code and the unique identifier of the patient to an external module requesting access to the medical records of the patient. The method also includes receiving the medical records of the patient and decrypting the medical records of the patient using the assigned encryption key of the patient.

BRIEF DESCRIPTION OF THE DRAWINGS

FIG. 7 illustrates a method for managing medical information in accordance with an embodiment of the present invention.

FIG. 8 illustrates an example personal health record (PHR) database for a data center.

Figure 1:
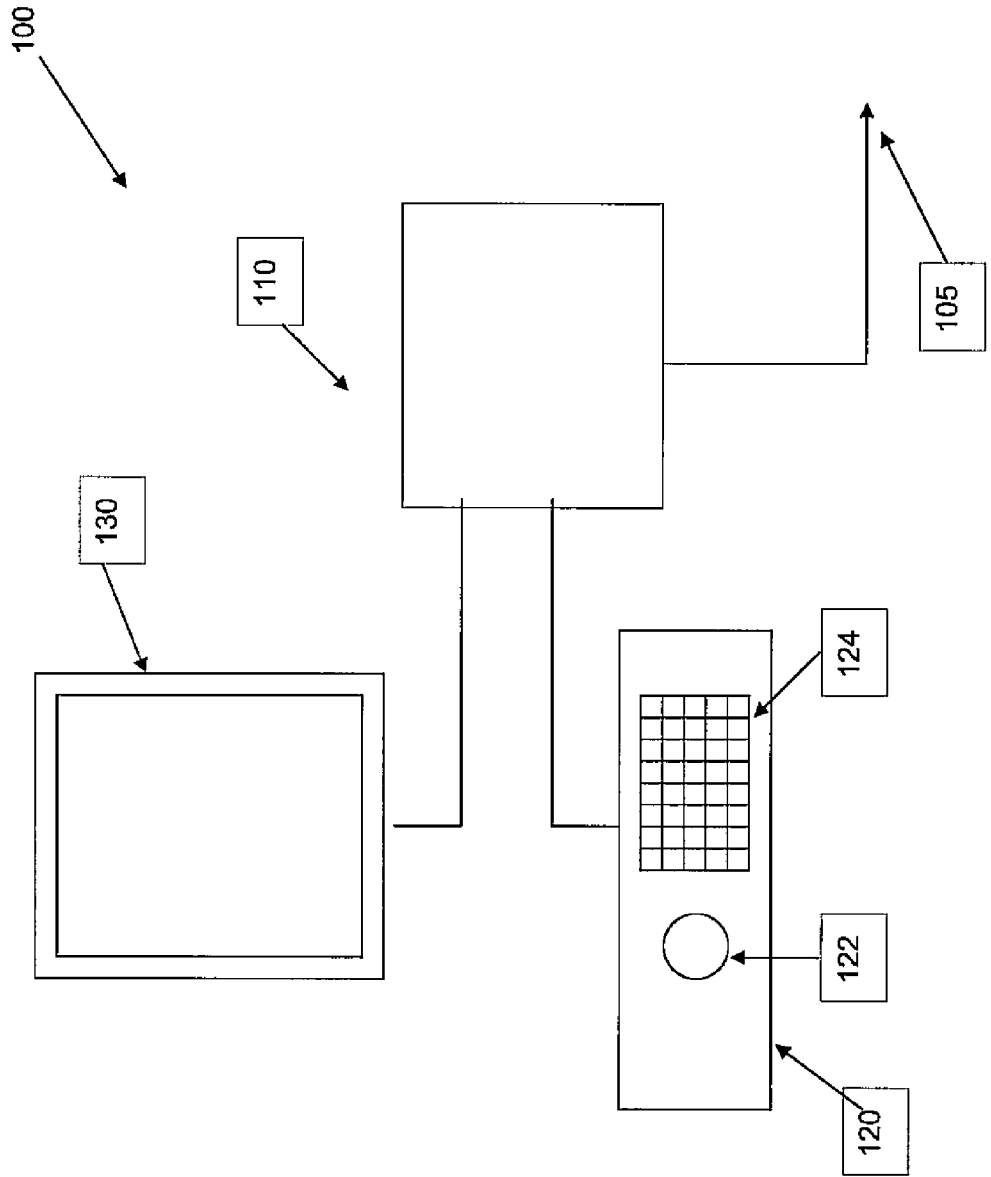
FIG. 1 illustrates a system for acquiring and communicating information in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a system 100 for acquiring and communicating information in accordance with an embodiment of the present invention. The system 100 includes a computer unit 110. The computer unit 110 may be any equipment or software that processes electronic data. For example, the computer unit 110 may be a personal computer. The computer unit 110 may have at least one processor and memory. The computer unit may receive input from a user. The computer unit 110 may be connected to other devices as part of an electronic network. In FIG. 1, the connection to the network is represented by line 105. The computer unit 110 may be connected to network 105 physically, by a wire, or through a wireless medium.

The system 100 also includes an input unit 120. The input unit 120 may be a console having a track ball 122 and keyboard 124. Other input devices may be used to receive input from a user as part of the input unit 120. For example a microphone may be used to receive verbal input from a user. The system 100 also includes at least one display unit 130. The display unit 130 may be a typical computer display unit. The display unit 130 may be in electrical communication with the computer unit 110 and input unit 120. In an embodiment, the display unit 130 may represent multiple display units or display regions of a screen. Accordingly, any number of display units may be utilized in accordance with the present invention. The computer unit 110 and display unit 130 may be separate units or be part of a single unit. In the case of separate units, the display unit 130 may be in electrical communication with the computer unit 110. The components of the system 100 may be single units, separate units, may be integrated in various forms, and may be implemented in hardware and/or in software. The system 100, or some variation thereof, may be used by a patient to access patient medical information and the system 100 may also be used by a clinic to access patient medical information.

Figure 2:
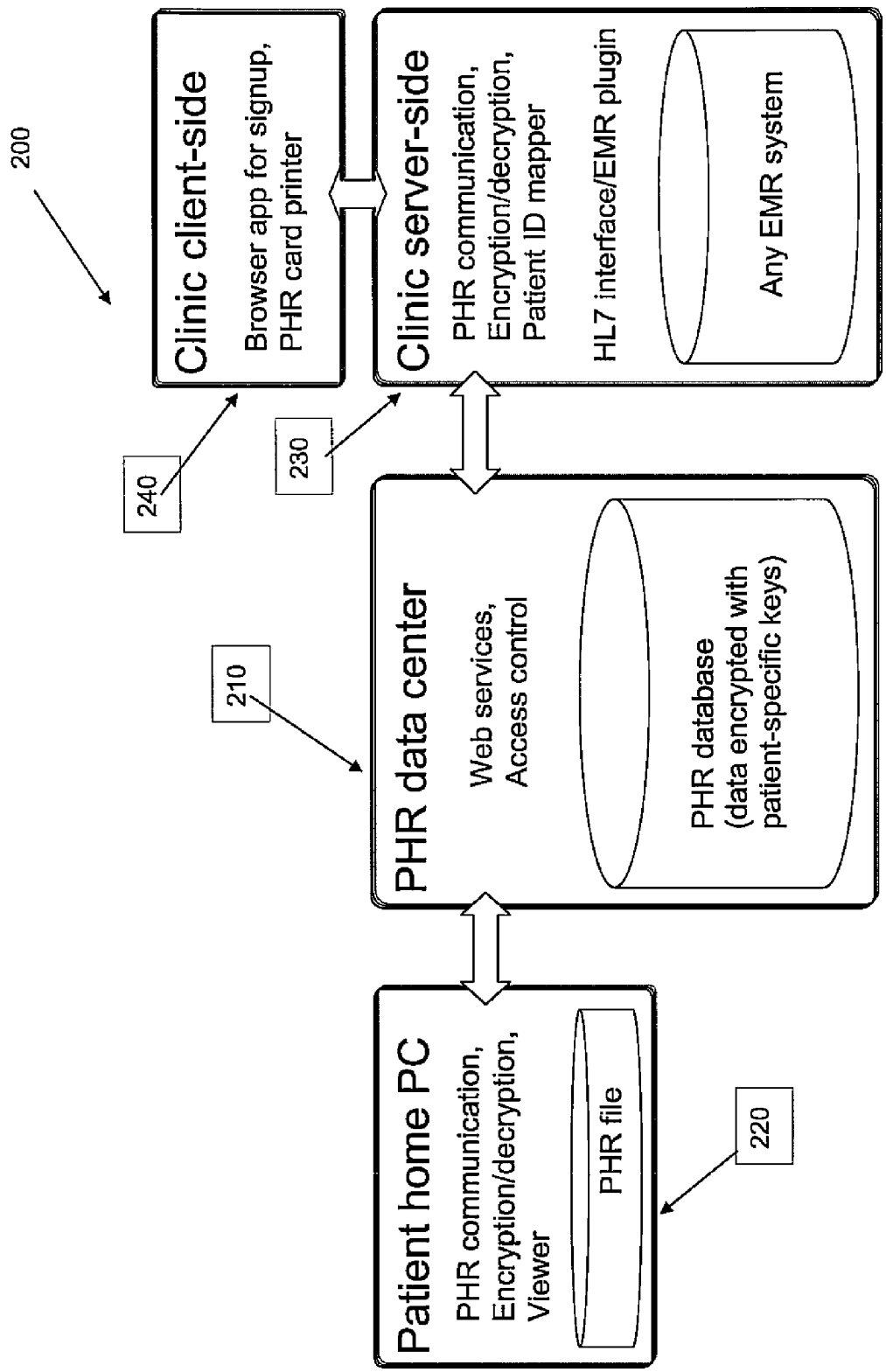
FIG. 2 illustrates a system for managing medical information in accordance with an embodiment of the present invention.

FIG. 2 illustrates a system 200 for managing medical information in accordance with an embodiment of the present invention. The system 200 includes a data center 210, a patient interface 220, a clinical server 230, and a clinical client 240. In an embodiment, the data center 210 is a database and/or other data store for storing patient medical record data and associated audit logs in encrypted form, accessible to the patient as well as authorized medical clinics (including hospitals, doctor's offices, and/or other diagnosis/treatment facilities). In an embodiment, the data center 210 may be a server or a group of servers and/or reside on a server or group of servers, for example. The data center 210 may also be one server or group of servers that is connected to other servers or groups of servers at separate physical locations. The data center 210 may represent single units, separate units, or groups of units in separate forms and may be implemented in hardware and/or in software. In an embodiment, the data center 210 receives medical information from a plurality of sources. For example, the sources of medical information may include various clinics, labs, pharmacies, as well as the patient him/herself.

In an embodiment, the data center 210 may represent a central database for storing encrypted update-transactions for patient medical records, including usage history. In an embodiment, the data center 210 also stores the patient medical records. The data center 210 stores and controls access to encrypted information. In an embodiment, medical records may be stored without using logic structures specific to medical records. In such a manner the data center 210 is not searchable. For example, a patient's data may be encrypted with a unique patient-owned key at the source of the data. The data is then uploaded to the data center 210. The data center 210 does not store unencrypted data thus minimizing privacy concerns. The patient's data may be downloaded to, for example, a computer unit and decrypted locally with the encryption key. In an embodiment, accessing software, for example software used by the patient and software used by the medical clinic performs the encryption/decryption.

As illustrated, for example, in FIG. 8, the data center 210 may include a personal health record (PHR) database 800. As shown, for example, in FIG. 8, the database 800 may be structured according to clinic, patient, patient/clinic association, and document. Clinic information 810 may include, for example, an identifier, a name, and address, a public key, and one or more security categories. Patient information 820 may include, for example, an identifier, a password hash, and an encrypted email address. Patient/clinic association information 830 may include a clinic identifier, a patient identifier, an encrypted key, and one or more override security categories. Document information 840 may include an identifier, a patient identifier, a clinic identifier, a security category, and encrypted data, for example.

The data center 210 may maintain a registration of patients and a registration of medical clinics. Medical clinics may be registered in the data center 210 with name, address, and other identifying information. The medical clinics are issued an electronic key that is associated with a certificate. The medical clinics are also granted a security category. The security category is typically based on clinic type. In an embodiment, the requests and data sent from medical clinics are digitally signed with the clinic's certificate and authenticated by the data center 210. Patients may be registered in the data center 210 with a patient identifier and password hash, without any identifying information. Typically, registered patients are issued a token containing a unique patient identifier and encryption key. The token may be, for example, a paper card, a magnetic card, a fob card, or some other equipment that may be used to identify the patient. A patient may access the data center 210 utilizing their token, and in an embodiment, a user identifier and password.

The data center 210 is in communication with the patient interface 220 and the clinical server 230. The data center 210, patient interface 220, and clinical server 230 may be in communication via any computer hardware and/or software that may process electronic communications to/from the data center 210, patient interface 220, and/or clinical server 230. For example, communication may include the computer unit 110, as shown in FIG. 1. In an embodiment, communication may occur using a card reader unit. The card reader unit may be a magnetic card reader that may process data when a magnetic card is passed through a receptacle, for example. In addition the card reader unit may receive communication from other types of devices, such as for example a fob card, universal serial bus flash memory, or other type of memory equipment and/or software.

The user may download a medical record from the data center 210, decrypt the medical record on the patient interface 220, such as a personal or handheld computer, and then process the data on a local basis, for example.

Similarly, a clinical client interface 240 may be used to download medical record information from the clinical server 230 and/or data center 210. For example, medical record information may be stored on the clinical server 230, such as in an electronic medical record (EMR) system and be accessible by the clinical client 240 from the server 230. As another example, medical record information may be stored at the data center 210 and may be accessible by the clinical client 240 via the clinical server 230, which requests the information from the data center 210.

In certain embodiments, one or more of the patient interface 220, clinical server 230, and/or clinical client 240 may be used to send data to the data center 210 for medical record update. Alternatively and/or in addition, sources such as laboratory results, pharmaceutical information, patient examination information, and image acquisitions, may provide data for storage at the data center 210. In certain embodiments, a patient may register or log in in association with a patient identifier. Data may then be encrypted using the patient identifier and patient encryption key and sent to the data center 210 to update the patient's medical record. Also, the data may be normalized prior to sending to the data center 210.

In an embodiment, data center 210, patient interface 220, clinical server 230, and/or clinical client 240 may be connected to one or more of each other via network connections, for example through the Internet or private network.

Figure 3:
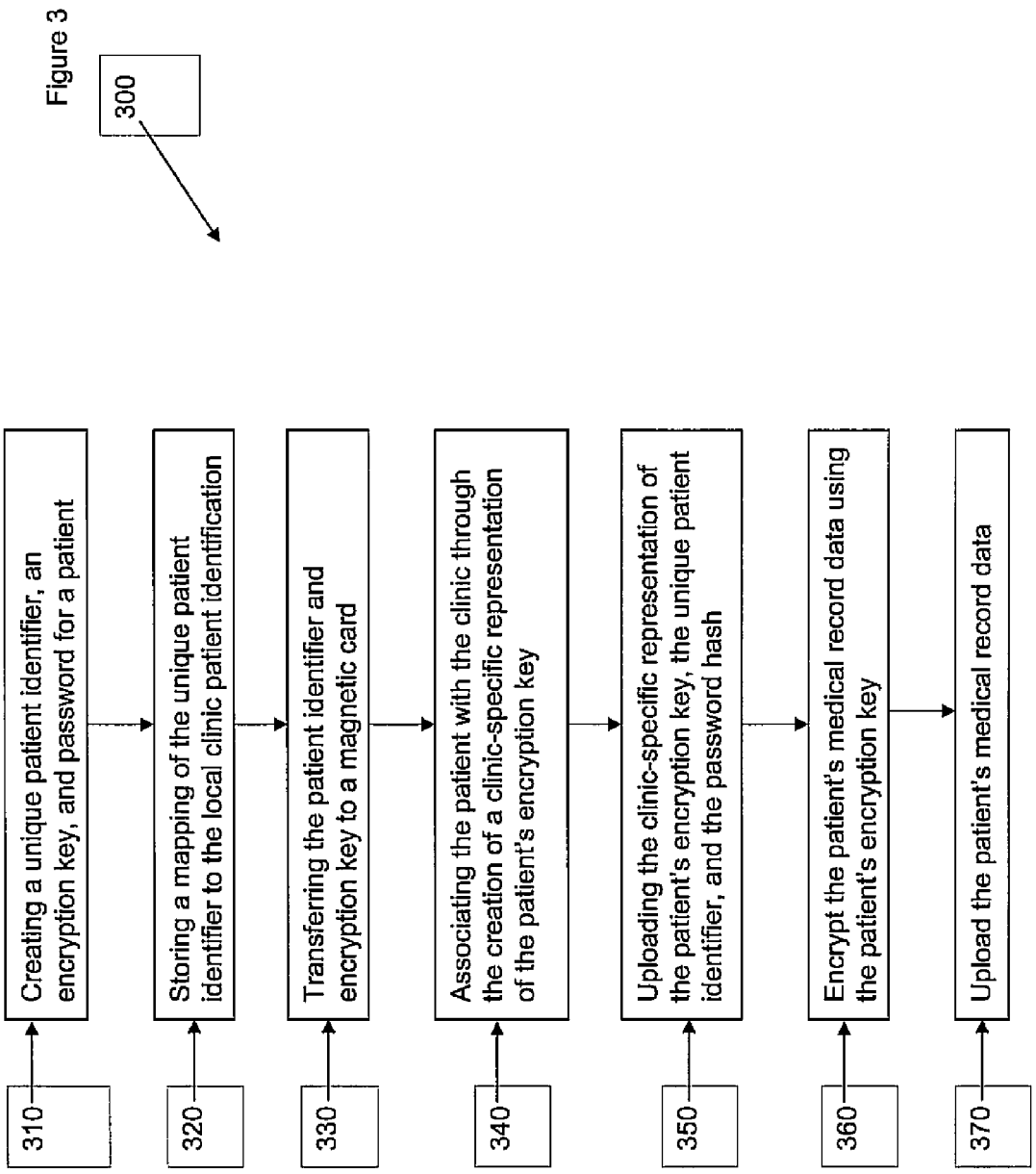
FIG. 3 illustrates a method for managing medical information in accordance with an embodiment of the present invention.

FIG. 3 illustrates a method 300 for managing medical information in accordance with an embodiment of the present invention. The method 300 illustrates a method that is performed upon an initial encounter with the patient and typically the patient does not yet possess a medical card. In an embodiment a patient visits a clinic, for example to receive medical treatment. At step 310, computer software typically executing on a computer at the clinic generates a unique patient identifier, a unique encryption key, and password for the patient. In an embodiment, the unique encryption key is a symmetric encryption key in that the same encryption key is used for encryption and decryption. At step 320, the unique patient identifier is mapped with the patient identifier used by the local clinic. The mapping is locally stored by the clinic. At step 330, the patient identifier and encryption key are transferred onto a medical paper card or magnetic card. Alternatively, the patient may be issued a fob card or other type of device. The medical card allows the patient to control and access their own medical record. At step 340, the patient is associated with the clinic through the creation of a clinic-specific representation of the patient's encryption key. In an embodiment, the patient is associated with the clinic through the creation of the clinic-specific representation by encrypting the patient's encryption key with the clinic's public key. In an embodiment, the clinic's public key is part of a public/private key pair used for asymmetric encryption. A first key may be used to encrypt and a second key may be used to decrypt. For example, the first key may be a public key that is used if one wants to ensure only the owner of the private key has access. The owner of the private key may encrypt with the private key to authenticate that a message originated from the owner. The clinic-specific representation of the patient's encryption key may then be stored in a database. The clinic-specific representation allows the clinic the ability to access the patient's medical records without storing the patient's encryption key locally or possessing the patient's medical card. At step 350, the clinic-specific representation of the patient's encryption key, the patient identifier, and the password hash are uploaded to a database or other server/storage type unit. In an embodiment, the database stores the clinic-specific representation of the patient's encryption key, the unique patient identifier, the password hash, and the associated clinic information. At step 360, the patient's medical record data is encrypted using the patient's encryption key. In an embodiment, the medical record data is encrypted by computer software operating on equipment at the clinic. At step 370, the encrypted medical record data is uploaded to a database or other server/storage type unit. The encrypted medical record data is stored at the database. In an embodiment, the medical record data may be optionally tagged with a security category. The tagging of the medical record data with a security category provides a layer of security in that a clinic without the appropriate security privileges cannot download the tagged medical record data. In an embodiment, a clinic that is associated with the patient may not download the tagged medical record data if the clinic does not have the appropriate security privileges.

Figure 4:
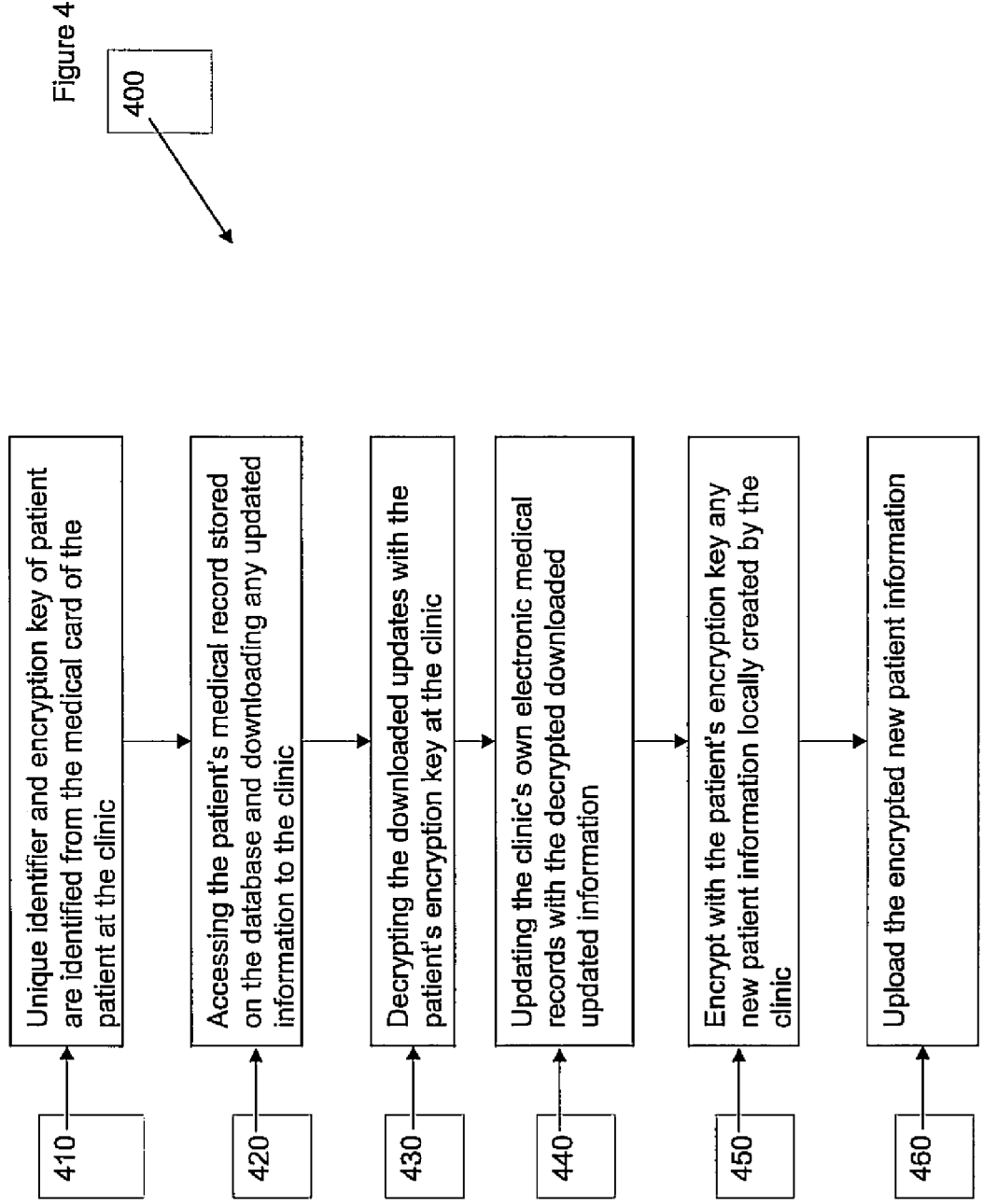
FIG. 4 illustrates a method for managing medical information in accordance with an embodiment of the present invention.

FIG. 4 illustrates a method 400 for managing medical information in accordance with an embodiment of the present invention. The method 400 illustrates a method that is performed upon a typical encounter with the patient after the patient has been issued a medical card. At step 410, the unique identifier and encryption key of a patient are identified from the medical card of the patient at the clinic. In an embodiment, the patient may swipe their medical card at the reception area of the clinic. The medical card may be processed by computer software at the clinic. Optionally, a tablet device may be used at the front desk to capture patient consent for various security clearances or confirmations. Alternatively, the unique identifier and encryption key of a patient are located by the clinic. In an embodiment where the clinic does not have a card reader or when the patient does not have access to his card, the clinic may look-up the unique patient identifier using the mapping stored locally. The clinic may obtain the patient encryption key by downloading the encrypted version of the key from the database and decrypting it using the private key of the clinic.

At step 420, the clinic may access the patient's medical record stored on the database. The clinic may send a download request containing the unique patient identifier. In an embodiment, the download request is digitally signed with the clinic's private key allowing the database to check the signature using the registered public key of the clinic. The database may also check the registered security categories of the clinic and disallow downloads for any patient record transactions for which the clinic does not have adequate security privileges. The clinic may then download any updated medical record information in encrypted form. At step 430, the downloaded updates are decrypted with the patient's encryption key. In an embodiment, the downloaded updates are decrypted by computer software executing on a computer at the clinic. At step 440, the new downloaded information that has been decrypted is used to update the clinic's own electronic medical records. At step 450, any new patient information that has been created locally by the clinic is encrypted with the patient's encryption key. At step 460, the encrypted data is uploaded to the database. In an embodiment, the computer at the clinic may be set to upload new information on a regulated schedule, such as on a nightly basis. In an embodiment, the new information may be optionally tagged with a security category. The tagging of the new information with a security category provides a layer of security in that a clinic without the appropriate security privileges cannot download the tagged new information. In an embodiment, a clinic that is associated with the patient may not download the tagged new information if the clinic does not have the appropriate security privileges. In an embodiment, a clinic server sends an email and/or other electronic communication alerting a patient that new information is available (e.g., lab results).

In an embodiment, a patient may be referred from a first clinic to a second clinic. The second clinic may desire to view the patient's medical record before the patient checks-in to the second clinic. In such a scenario, the first clinic may download the public key of the second clinic and use the public key of the second clinic to encrypt the patient's encryption key. The first clinic may upload the encrypted key of the patient, creating an association between the patient and the second clinic. Once the second clinic has retrieved the patient's key, the second clinic may download the patient's medical record prior to the patient's arrival.

In an embodiment, the scenario of a patient being separated from his medical card is contemplated. For example, a patient may lose his medical card. The medical card is typically not usable if found by another person because the finder of the medical card does not have the password. In the embodiment of the lost medical card, the patient may report the lost card to the clinic. The clinic may download the encrypted key of the patient and decrypt the patient's key with the clinic's private key. The clinic may issue a new medical card to the patient. For increased security, the clinic may also change the encryption key of the patient. In order to change the encryption key of the patient, the clinic may download the available transactions for the patient. The clinic may generate a new encryption key for the patient. The clinic may decrypt the available transactions with the old patient key and re-encrypt the available transactions with the new patient key. The clinic may then upload the available transactions to a database. The clinic may then download the public keys for the clinics associated with the patient. For the associated clinics, the new patient key is encrypted with the respective clinic's public key. The clinic may then upload the new clinic-specific encrypted patient keys.

Figure 5:
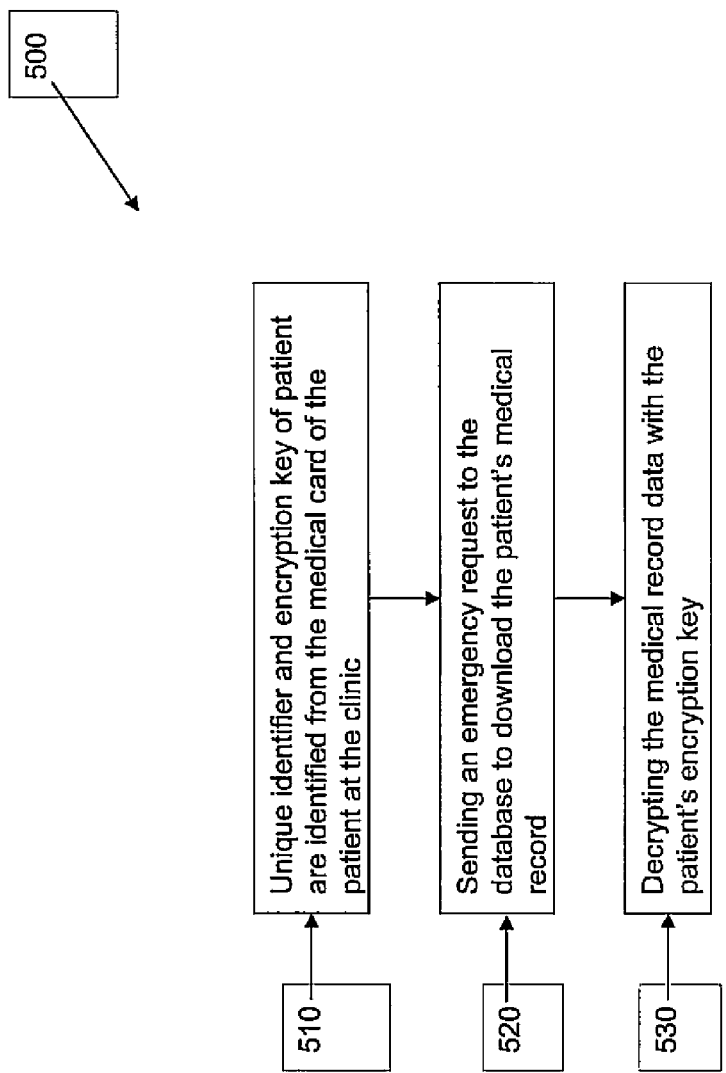
FIG. 5 illustrates a method for managing medical information in accordance with an embodiment of the present invention.

FIG. 5 illustrates a method 500 for managing medical information in accordance with an embodiment of the present invention. The method 500 illustrates a method that is performed upon an emergency encounter with the patient, for example an unconscious patient is brought into an emergency clinic and the emergency clinic is not associated with the patient. If the patient is carrying his or her medical card, the method 500 may be performed. At step 510, the unique identifier and encryption key of the patient are identified from the medical card of the patient. In an embodiment, an emergency medical technician or other health care professional may "swipe" the medical card of the patient. Computer software may receive the information from a card reader. In an embodiment, an emergency medical technician may have a wireless tablet computer with the ability to read magnetic cards. The emergency medical technician may access the medical records of the patient prior to arriving at the emergency clinic. At step 520, after the medical card has been "swiped" the health care professional may send an emergency request to the database using computer software to download the patient's medical record. The emergency request may be a code provided to emergency care providers that enables the emergency care providers to access a patient's medical records if the emergency care provider has the patient's encryption key and unique identifier. At step 530, computer software at the emergency clinic decrypts the medical record data with the patient's encryption key. The emergency clinic then has access to the patient's medical records and can make a more efficient and accurate diagnosis.

Figure 6:
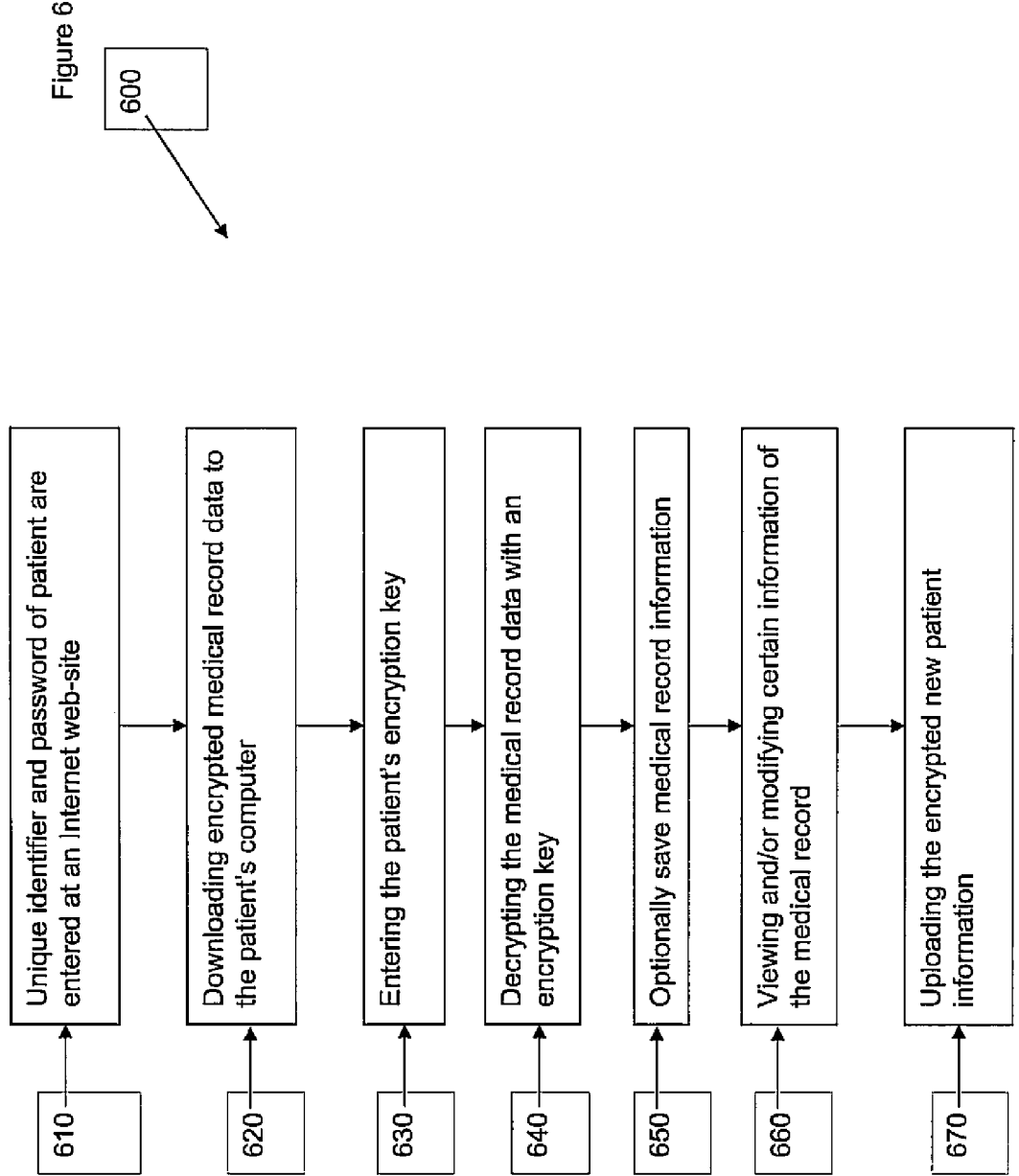
FIG. 6 illustrates a method for managing medical information in accordance with an embodiment of the present invention.

FIG. 6 illustrates a method 600 for managing medical information in accordance with an embodiment of the present invention. The method 600 illustrates a method that is performed when the patient requests access to their medical records through a computer. For example, the patient may desire to access their medical records using a personal computer at home. At step 610, in an embodiment the patient enters the patient identifier and password at an Internet website. At step 620, the encrypted medical record data is downloaded to the patient's computer. At step 630, the patient's encryption key is entered. In an embodiment, the patient may store the encryption key on a local disk for convenience. Alternatively, the patient's computer may have a magnetic card reader. The patient may enter the encryption key using the magnetic card reader or other device. At step 640, the medical record data is decrypted using the encryption key. At step 650, the patient may optionally save the medical record information on a local disk for offline access. At step 660, the patient may view and/or modify certain information of the medical record. For example, the patient may view their medical records and history. In an embodiment, the patient does not have the ability to modify the entries from clinics or other sources. The patient may add comments or modify security clearances. For example, the patient may add comments regarding the side effects of certain medications. The patient may also modify the access rights of certain clinics. For example, the patient may revoke a clinic's access rights by disassociating the patient from the clinic. The patient may modify a clinic's access rights by overriding the default security categories. The patient may request a clinic or other source upload any new information. The patient can acknowledge the receipt of laboratory results or other clinical information. At step 670, the patient may upload any modified information using the assigned encryption key.

FIG. 7 illustrates a method 700 for managing medical information in accordance with an embodiment of the present invention. The method 700 illustrates a method that is performed when the patient logs into a website to access medical information. The website may present the patient with the option of receiving health information in context of the patient's medical information. For example, computer software/instructions may execute to process the medical information available in the data center 210 for a medical patient and return information about the conditions of the patient to the patient.

For example, at step 710, in an embodiment the patient enters the patient identifier and password at an Internet website. The patient identifier and password grant the patient access to a set of tools. Tools and/or other functionality available to a patient via a website and/or via the patient's computer (e.g., the patient interface 220) include matching technology/tools, education/information, guided feedback, etc. At step 720, a patient may select a tool to process their medical information. At step 730, the patient data is decrypted. Accordingly the patient may download the medical record from the database 210, decrypt the medical record on the patient's computer and execute the computer software on the patient's computer.

At step 740, a processor executes program code according to a selected tool and/or other functionality. For example, the processor may execute program code to perform a recommended care plan algorithm. The recommend care plan algorithm receives data from the patient's medical record and processes the data. Based on the data available, the recommended care plan algorithm outputs a recommended care plan for the patient. The recommended care plan algorithm may identify, among other things, the patient's conditions and degree of severity of the conditions. The recommended care algorithm may also consider data such as sex, age, height, weight, heredity, lifestyle factors, activity level, and/or other factors. The recommended care plan algorithm may utilize these factors and provide a recommended care plan. The recommended care plan may include techniques for improved health based on the patient's condition. For example, the recommended care plan may include diet recommendations to an individual that has been diagnosed with diabetes.

At step 750, in an embodiment, a memory includes program code executable by the processor for providing a recommendation or other output based on selected tool or other functionality. For example, program code executes to recommend a care plan based on the results of the recommended care plan algorithm. The recommended care plan may include techniques for improved health based on the patient's condition. For example, the recommended care plan may include diet recommendations to an individual that has been diagnosed with diabetes. The recommended care plan is typically customized to the patient and provides recommendations and information based on the specific health of the patient as opposed to generalized information.

As an alternative example, at step 740, the memory includes program code executable by a processor for performing a sponsored information algorithm. In such an embodiment, step 710 is executed as described above. In an embodiment, step 720 is not executed as the sponsored information handling may be automatic. The patient may not select an algorithm tool. Step 730 is executed as described above. At step 740, the sponsored information algorithm receives data from the patient's medical record and processes the data. Based on the data available, the sponsored information algorithm outputs sponsored information for the patient. At step 750, the memory includes program code executable by the processor for providing sponsored information based on the results of the sponsored information algorithm. The sponsored information may include educational material, product/service offerings, or other advertisements, for example.

In operation and for example, a patient that has recently been diagnosed with diabetes may receive information from the treating physician. The physician may log the diagnosis and treatment specifics in the patient's electronic medical record. In addition, various tests and laboratory information may be recorded as part of the patient's electronic medical record, or may be recorded separately. Similarly, the pharmaceutical information may be recorded as part of the patent's electronic medical record or may be recorded separately. In an embodiment, the medical information is sent to the data center 210. In an embodiment, the medical information is normalized by the sources of the information prior to sending to the data center.

Certain embodiments above may be applied to an architecture and components based upon Health Information Exchange (HIE) standards, such as document storage, querying, etc.

Certain embodiments provide Web portal applications for data presentation to patients. A Web-based portal can provide an adaptive and proactive experience for users including matching technology/tools, education/information, and guided feedback based upon a patient's specific personality and lifestyle assessment, for example.

The systems and methods described above may be carried out as part of a computer readable storage medium including a set of instructions for a computer. The computer readable storage medium may include single units, separate units, may be integrated in various forms, and may be implemented in hardware and/or in software.

A technical effect of the invention is to manage consumer health in a personalized consumer healthcare context. In an embodiment of the present invention, the technical effect may be achieved by acquiring information regarding a patient in a centralized manner. A centralized system stores patient medical record data and associated audit logs in encrypted form accessible to the patient as well as authorized medical clinics. Typically, software used by the patient and software used by the medical clinic would be responsible for the encryption/decryption minimizing privacy concerns. Furthermore, the information is normalized to a standard format.

Certain embodiments provide a personal health record system and method of access that improves patient privacy. If patient data is handled as clear, unencrypted text at the data center at any point, the data is subject to many types of security risks. Maintaining data encryption at the data center and providing secure methods for data encryption and/or decryption on the authorized patient and/or clinical access side helps to improve security and reliability of an expansive personal health record system.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for a patient to access medical record data of said patient, said medical record data including one or more entries from a clinic, said method comprising:

registering said patient to access said medical record data, said registering comprising:
creating a unique patient identifier for said patient and assigning an encryption key to said patient;
storing a mapping of said unique patient identifier to a local clinic patient identification of said clinic;
associating said patient with said clinic by creating a clinic-specific representation of said encryption key;
transmitting the clinic-specific representation of said encryption key and the unique patient identifier to an external memory;
encrypting said medical record data using the encryption key assigned to said patient; and,
transmitting the medical record data, said medical record data being encrypted with said encryption key assigned to said patient;

receiving, by a patient computer, a patient identifier and password to authenticate said patient;

receiving, by said patient computer, the encrypted medical record data from an external source and saving said encrypted medical record data to a personal health record arranged in a local memory at said patient computer;

receiving, by said patient computer, a unique encryption key assigned to said patient;

decrypting, by said patient computer, said encrypted medical record data with said unique encryption key assigned to said patient, wherein said encrypted medical record data is not decrypted at said external source but instead in said local memory at said patient computer;

displaying at said patient computer said medical record data to said patient and locally receiving changes to said medical record data from said patient, wherein said patient is unable to modify said one or more entries from said clinic in said encrypted medical record data;

encrypting, by said patient computer, at least the changes to said medical record data with said unique encryption key assigned to said patient; and, communicating, via said patient computer, at least said encrypted changes to said medical record data to said external source from said patient computer, wherein said external source receives said encrypted changes but not unencrypted medical record data.

2. The method of claim 1, wherein said receiving a unique encryption key assigned to said patient includes receiving said encryption key from a token.

3. The method of claim 1, wherein said changes to said medical record data include the addition of comments entered by the patient.

4. The method of claim 1, wherein said changes to said medical record data include changing the access parameters of entities that may access said medical record data.

5. The method of claim 1, further comprising:
processing said medical record data of said patient using an algorithm including at least one of a recommended care plan algorithm and a sponsored information algorithm and
recommending an output based on the results of the algorithm, the output including at least one of a recommended care plan and sponsored information.

6. The method of claim 1, further comprising notifying the patient that new medical information is available.

7. The method of claim 1, further comprising generating at least one of an audit log and usage history for storage at said external source.

8. The method of claim 1, further comprising:
transferring said unique patient identifier and said encryption key assigned to said patient to a token.

9. The method of claim 1, further comprising receiving and transmitting updated information for the medical record data of said patient to said external source, said method comprising:
receiving updated information for said medical record data of said patient from a clinic associated with said patient and said external source;
decrypting the updated information with the assigned encryption key;
updating the medical record data of the patient that is stored in local memory with the decrypted updated information;

encrypting said updated medical record data with the assigned encryption key of said patient; and,
transmitting the encrypted updated medical record data to said external source.

10. The method of claim 1, wherein said external source comprises a data center.

11. A non-transitory computer-readable storage medium including program code which, when executed by a processor, implements a method for patient access to medical record data, said medical record data including one or more entries from a clinic, said method comprising:
registering said patient to access said medical record data, said registering comprising:
creating a unique patient identifier for said patient and assigning an encryption key to said patient;
storing a mapping of said unique patient identifier to a local clinic patient identification of said clinic;
associating said patient with said clinic by creating a clinic-specific representation of said encryption key;
transmitting the clinic-specific representation of said encryption key and the unique patient identifier to an external memory;
encrypting said medical record data using the encryption key assigned to said patient; and,
transmitting the medical record data, said medical record data being encrypted with said encryption key assigned to said patient;
receiving a patient identifier and password to authenticate said patient;
receiving the encrypted medical record data from an external source and saving said encrypted medical record data to a personal health record arranged in a local memory at a patient computer;
receiving at said patient computer a unique encryption key assigned to said patient;
decrypting, at said patient computer but not at said external source, said encrypted medical record data with said unique encryption key assigned to said patient, wherein said encrypted medical record data is not decrypted at said external source but instead in said local memory at said patient computer;
displaying at said patient computer said medical record data to said patient and locally receiving changes to said medical record data from said patient, wherein said patient is unable to modify said one or more entries from said clinic in said encrypted medical record data;
encrypting at said patient computer at least the changes to said medical record data with said unique encryption key assigned to said patient; and,
communicating at least said encrypted changes to said medical record data to said external source from said patient computer, wherein said external source receives said encrypted changes but not unencrypted medical record data.

* * * * *